United States Patent [19]

Franklin et al.

[11] Patent Number: 5,641,813
[45] Date of Patent: Jun. 24, 1997

[54] COSMETIC COMPOSITION

[75] Inventors: Kevin Ronald Franklin, Wirral; Susan Mary Houghton, Warrington; Ian Gardner Lyle, Clywd, all of United Kingdom

[73] Assignee: Chesebrough-Pond's USA Co., Division of Conopco, Inc., Greenwich, Conn.

[21] Appl. No.: 565,354

[22] Filed: Nov. 30, 1995

[30] Foreign Application Priority Data

Dec. 2, 1994 [GB] United Kingdom ............... 9424445

[51] Int. Cl.$^6$ .................................... A61K 7/42
[52] U.S. Cl. ............ 514/721; 514/553; 514/557; 514/560; 514/844; 514/847; 514/944; 424/400; 424/401; 424/688; 556/170; 556/182; 562/589; 562/579
[58] Field of Search .......................... 514/557, 721

[56] References Cited

U.S. PATENT DOCUMENTS

| | | | |
|---|---|---|---|
| 5,073,573 | 12/1991 | Martin et al. | 514/844 |
| 5,169,967 | 12/1992 | Assmus et al. | 554/71 |
| 5,474,762 | 12/1995 | Carr et al. | 424/59 |
| 5,520,918 | 5/1996 | Smith | 514/847 |

FOREIGN PATENT DOCUMENTS

| | | |
|---|---|---|
| 0 318 642 | 6/1989 | European Pat. Off. . |
| 0 419 759 | 4/1991 | European Pat. Off. . |
| 0 557 089 | 8/1993 | European Pat. Off. . |
| WO94/10972 | 5/1994 | WIPO . |
| WO94/10973 | 5/1994 | WIPO . |
| WO95/05150 | 2/1995 | WIPO . |

OTHER PUBLICATIONS

Meyn, M. et al., "Anion–Exchange Reactions of Layered Double Hydroxides", *Inorg. Chem.*, 1990, vol. 29, pp. 5201–5207.
Meyn et al, "Anion–Exchange Reactions of Hydroxy Double Salts", *Inorg. Chem.*, 1993, vol. 32, pp. 1209–1215.
Merck Index, 10th edition, 1983, #5173.
Merck Index, 10th edition, 1983, #9471.

*Primary Examiner*—Rebecca Cook
*Attorney, Agent, or Firm*—Rimma Mitelman

[57] ABSTRACT

A cosmetic composition comprising a hydroxy material selected from;

a) layered double hydroxides of formula

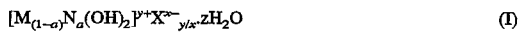

b) a hydroxy salt of formula

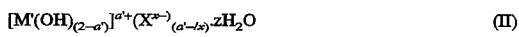

2 Claims, No Drawings

COSMETIC COMPOSITION

The present invention relates to a cosmetic composition. In particular, it relates to a cosmetic composition comprising a hydroxy material selected from layered double hydroxides and hydroxy salts, which are suitable for treating the skin and delivering thereto benefit agents.

Layered double hydroxides of formula

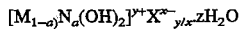

where

M is selected from divalent metal ions and lithium;
N is a trivalent metal ion;
X is an anion of charge x−;
y+ is the net charge on the mixed metal hydroxide cation; and when M is a divalent metal ion "a" is a number from 0.17 to 0.5 and y=a; and when M is lithium "a" is a number from 0.67 to 0.75 and y=(2a−1); and
z is a number from 0 to 10;

and water-insoluble hydroxy salts of formula

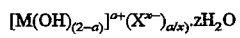

where

M is at least one divalent metal ion;
a is a number in the range 0.05 to 1;
x is the charge on the anion; and
z is a number from 0 to 10;

are, respectively, described in Meyn et al., Inorganic Chemistry, 29, 5201 (1990) and 32, 1209 (1993).

In both of these structures the metal ions occur in layers in which the metal ions are connected together through the OH groups and the anions X, are located in interlayers between layers of metal ions. Furthermore, it is known that X can undergo ion exchange to be replaced by other anions eg organic anions.

Aluminium magnesium hydroxy fatty acid compounds of formula

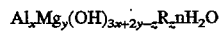

where R is an aliphatic monocarboxylate containing between 12 and 22 carbon atoms;
x=2
Z≦y≦10
z=2 and n is an integer greater than zero
and their use in cosmetic and pharmaceutical preparations together with organic lipophilic compounds is known from EP 419 759.

Various applications for these types of hydroxy materials have been described in the scientific literature, notably including their use as chemical catalysts.

The hydroxy materials can be used as sunscreen agents in sunscreen compositions if at least some of anions display ultraviolet absorption over at least a portion of the UV wavelength range, 290 to 400 nanometers. Such materials are described in PCT/EP 94/02669 and European Patent Specification No. 557089.

According to WO 94/10972 cosmetic compositions comprising specific Zn/Al layered double hydroxides have been found to have antimicrobial activity.

Applicants in their search for systems which deposit benefit agents, for example moisturising and conditioning agents, onto skin have unexpectedly found that the aforementioned hydroxy materials can be employed in a cosmetic composition to deliver the benefit agents.

Thus, according to the invention there is provided a cosmetic composition comprising a hydroxy material selected from;

a) layered double hydroxides of formula

 (I)

where

M is selected from divalent metal ions and lithium;
N is a trivalent metal ion;
X is an anion of charge x−;
y+ is the net charge on the mixed metal hydroxide cation; and
when M is a divalent metal ion "a" is a number from 0.17 to 0.5 and y=a;
when M is lithium "a" is a number from 0.67 to 0.75 y=(2a−1); and
z is a number from 0 to 10; and b) a hydroxy salt of formula

 (II)

where

M' is at least one divalent metal ion;
a' is a number in the range 0.05 to 1;
X is an anion of charge x−; and
z is a number from 0 to 10; and c) mixtures thereof; and wherein at least some of X comprises the anionic form of a non-sunscreen skin benefit agent.

Preferably x is other than an aliphatic monocarboxylate having 12 to 22 carbon atoms.

The invention also relates to the use of the hydroxy material as hereinbefore defined to deliver benefit agents to skin treated therewith.

Hydroxy materials as hereinbefore defined can be preformed before formulating into a cosmetic composition. Alternatively, they can be formed in situ in the composition as a result of interaction of an hydroxy material where X is an anion other than that derived from a skin benefit agent, and such as nitrate, chloride and sulphate, with a skin benefit agent.

The hydroxy materials of the present invention are macromolecules and, therefore, when they have deposited they are not prone to penetrating the skin.

Included amongst the skin benefit agents are those materials which condition the skin (stratum corneum) and keep it soft by retarding the decrease of its water content and/or protect the skin. Preferably the skin benefit agent is selected from anti-ageing agents such as alpha-hydroxy acids, examples of which are glycolic, lactic and alpha-hydroxycaprylic acid, anionic derivatives and salts thereof such as lactates, glycolates, acyl lactylates and acyl glycolates; moisturising agents such as pyrrolidine carboxylic acid and amino acids; organic antimicrobial agents such as 2,4,4'-trichloro-2-hydroxy diphenyl ether (triclosan) and benzoic acid; anti-acne agents such as azelaic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Where the skin benefit agent is in an acid form it must be readily ionisable to give an anionic species.

Preferably the hydroxy material is present in the composition of the invention in an effective amount, ie from 0.1 and up to 100% by weight of the composition, in the case of powders. Without being bound by theory, it is believed the hydroxy material releases the skin benefit agent by at least three mechanisms:

i) ion exchange of the benefit agent with unwanted sebaceous acid or anions on the skin;

ii) sebaceous acids dissolving the hydroxy material thereby releasing the benefit agent; and iii) ion-exchange of skin benefit agent with chloride present in salt/sweat excreted from the human body.

During use of the cosmetic compositions according to the invention, in order to achieve maximum benefit the skin benefit agent should be released from the hydroxy material and delivered onto the skin being treated.

The cosmetic composition according to the invention is primarily intended as a personal care product for topical application to the skin and/or for cleansing the face. It may also be used for washing the hair as well as the whole body. The composition according to the invention is preferably used as a facial make-up eg. foundation, lipstick; face-pack; facial cleansing mask; facial cream, preferably a "leave-on" product; facial cleanser, which is generally a "wipe-off" or "rinse-off" product; facial wash foam; hair shampoo; body shampoo; bath foam; or shaving cream.

The cosmetic composition may take the form of a powder; or a liquid, gel or emulsion intended to be dispensed from a capped container such as a bottle or tube, a pep-operated or propellant driven aerosol dispenser; a solid such as a stick, bar or tablet to be used in a similar manner to a conventional soap bar.

Depending on the skin benefit agent, the hydroxy material may be suspended in an aqueous vehicle or in an oil phase. Water-in-oil and oil-in-water emulsions may be used. If the skin benefit agent is a lactate an aqueous system is preferred whereas when a $C_{12}$ alpha hydroxy acid is used an oil phase is preferred.

When the cosmetic composition according to the invention is in the form of emulsion it also comprises a cosmetically acceptable vehicle to act as a dilutant, dispersant or carrier for the hydroxy material and benefit agent. Suitable vehicles include water, oils and solvents such as ethyl alcohol. The cosmetically acceptable vehicle will preferably be present in an amount from 10 to 99.9% by weight of the emulsion and may, in the absence of other cosmetic adjuncts, form the balance of the composition.

When the composition is in the form of a powder it may comprise a carrier for example chalk, talc, fullers earth and kaolin.

When the cosmetic composition is intended as a facial cleanser, facial wash foam, hair shampoo, body shampoo, or bath foam, it preferably will be in the form of an aqueous liquid additionally comprising a surface active agent. The surface active agent can be selected from any known surfactant suitable for topical application to the human body such as amphoteric, nonionic and cationic surface active agents and mixtures thereof but excluding anionic surface active agents. This is because anionic surface active agents may undergo ion exchange with the hydroxy material.

Mild surfactants, ie. surfactants which do not damage the stratum corneum, the outer layer of skin, are particularly preferred.

Suitable amphoteric surface active agents have an alkyl or alkenyl group of 7 to 18 carbon atoms and comply with an overall structural formula

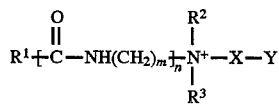

where $R^1$ is alkyl or alkenyl of 7 to 18 carbon atoms $R^2$ and $R^1$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and

Y is $—CO_2^-$ or $—SO_3-$

Within the above general formula are included simple betaines of formula:

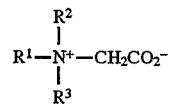

and amido betaines of formula:

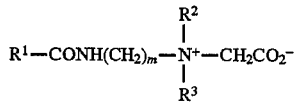

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is a sulphobetaine of formula:

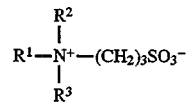

or

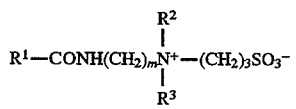

where m is 2 or 3, or variants of these in which $—(CH_2)_3SO_3^-$ is replaced by

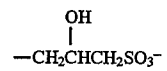

$R^1$, $R^2$ and $R^3$ in these formulae are as defined previously.

Suitable nonionic surface active agents include such as alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

The surfactant active agent is preferably present at a level of from 1 to 45 wt %, preferably 3 to 30 wt %.

The composition according to the invention may contain skin benefit agents in addition to those forming part of the hydroxy material.

Other typical optional components for including in the composition of the invention are opacifiers; preservatives such as sorbate; astringents such as menthol and ethanol; emollients such as polyoxyalkylene methyl glucosides; humectants such as glycerine; sorbitol and other polyhydroxy alcohols such as polyethylene glycol; suncreen agents such as octyl methoxyl cinnamate (Parsol MCX) and butyl methoxy benzoylmethane (Parsol 1789); perfumes; bactericides; colourants; antioxidants; skin-feel modifiers; and thickeners and structurants such as swelling clays and cross-linked polyacrylates eg Carbopol (TM) (polymers available from Goodrich).

Numerous methods for preparing layered double hydroxides have been described in the literature. One suitable method, for example, involves the treatment of a suspension of an oxide of one metal with a soluble salt, notably a nitrate, chloride or sulphate of another metal, preferably at an elevated temperature, followed by filtration of the solid material.

Preparation of the hydroxy salts of formula (II) have been described in the paper by Meyn, hereinbefore referenced, and, similarly, involves treating a suspension of zinc oxide with copper oxide or nitrate, preferably at an elevated temperature, followed by filtration of the solid material.

The hydroxy materials can be identified by chemical analysis for the elements present, and by X-ray diffraction.

Ion exchange to introduce the benefit agent into the hydroxy material is carried out by suspending the hydroxy material in an aqueous solution of the anions which it is desired to introduce into the structure. The process may be carried out at elevated temperatures to increase the speed of reaction. The final solid product is then filtered off and may be characterised by chemical analysis, infrared spectroscopy, and X-ray powder diffraction.

Different anions have different affinities for the interlayer site in the hydroxy materials. In the layered double hydroxides it has been found that organic anions are able to displace sulphate, chloride and nitrate anions; thus these organic anions can be incorporated into the layered double hydroxide by ion exchange. By contrast, carbonate ions will displace both the organic anions and the inorganic anions hereinbefore mentioned. Accordingly layered double hydroxides with carbonate as the interlayer anion should not be chosen as the starting material if the skin benefit agent is incorporated by ion-exchange.

Layered double hydroxides with carbonate anions may be used as starting materials if the skin benefit agent is introduced by an acid decomposition reaction as described by Reichle in Solid State Ionics 1986, vol 22 page 135 or by a thermal decomposition-reformation process as described by Chibwe and Jones, J. C. S Chem Comm. 1989, page 926.

The invention will now be described with reference to the following non-limiting examples.

EXAMPLES

Example 1 i) Preparation of Magnesium Aluminium Hydroxy Nitrate 46.8 g of magnesium oxide was suspended in 250 ml of distilled water in a one liter polypropylene screwcap bottle. 145.1 g of hydrated aluminium nitrate ($Al(NO_3)_3 \cdot 9H_2O$) was dissolved in 500 ml of distilled water and the resulting solution was added, with stirring, to the magnesium oxide suspension. The bottle was capped, shaken vigorously for 2 minutes and then placed in a thermostated oven for 5 days at 90° C. At the end of this period the solid was filtered off, washed thoroughly with water and then freeze dried. The dried material was finally equilibrated with water vapour by storing in a desiccator over a saturated sodium chloride solution.

The chemical composition of this material was determined by analysis. The results were as follows:

Mole ratio Mg/Al=2.0

% $MgO+Al_2O_3$=49.8

% $H_2O$ (from dehydroxylation)=16.7

% $NO_3$=23.2

This is consistent with a formula for the anhydrous material of

$Mg_4Al_2(OH)_{12}(NO_3)_2$

The X-ray diffraction pattern of the hydrated material showed i) the only crystalline material present was a layered double hydroxide analogous to hydrotalcite. Characteristic line spacings at 1.48 Å and 1.51 Å were present.

ii) there was a major line at 8.8 Å, which has been shown to be characteristic of this interlayer nitrate containing material.

ii) Preparation of Mg/Al hydroxy lactate 54.14 g of L-(+)-lactic acid was dissolved in 300 ml water and added to 24.00 g sodium hydroxide dissolved in 300 ml water. This solution was then added to 80 g of the nitrate formed in Example i) described above, in a 1 liter polypropylene bottle. The bottle was capped, shaken for 2 minutes and then heated at 90° C. for 18 hours. The solid was filtered off, washed with distilled water, and then freeze dried. The product was finally equilibrated with water vapour by storing it in a desiccator over a saturated sodium chloride solution.

The chemical analysis was as follows:

% $MgO+Al_2O_3$=46.51

% C=11.31

This is consistent with a formula for the anhydrous material of $Mg_4 Al_2 (OH)_{12} (lactate)_{1.78} (NO_3)_{0.22}$ The x ray diffraction pattern showed i) the only crystalline material present was a layered double hydroxide.

ii) there was a major line at 14.6 Å which was not present in the starting material.

IR Analysis of the product showed absorption peaks centred at 1140 $cm^{-1}$ and 1596 $cm^{-1}$ which were not present in the nitrate form starting material and are consistent with the presence of lactate ions.

iii) Preparation of Mg/Al hydroxy glycolate

Example 1 ii) was repeated except a solution comprising 45.6 g glycolic acid dissolved in 300 ml water and to 24.0 g of sodium hydroxide dissolved in 300 ml water was added to the nitrate formed in Example i)

The chemical analysis of the resulting product was:

% $MgO+Al_2O_3$=51.25

% C=9.23

This is consistent with a formula for the anhydrous material of $Mg_4 Al_2 (OH)_{12} (glycolate)_{1.97} (NO_3)_{0.03}$ The x ray diffraction pattern showed i) the only crystalline material present was a layered double hydroxide.

ii) there was a major line at 9.6 Å which was not present in the starting material.

IR analysis of the product showed absorption peaks centred at 1103 cm$^{-1}$ and 1608 cm$^{-1}$ which were not present in the nitrate form starting material and are consistent with the presence of glycolate ions.

iv) Preparation of Mg/Al hydroxy Triclosan (phenylate anion form).

Example 1 ii) was repeated except a solution comprising 10.86 g triclosan dissolved in 100 ml water and 1.5 g sodium hydroxide dissolved in 50 ml water was added to 10 g of the nitrate formed in Example 1 i) and the resulting mixture heated for 3 days instead of 18 hours.

The chemical analysis of the resulting product was:

% MgO+Al$_2$O$_3$=29.35

% C=25.60

This is consistent with a formula for the anhydrous material of Mg$_4$ Al$_2$ (OH)$_{12}$ (Triclosan)$_{1.5}$ (NO$_3$)$_{0.5}$ The x ray diffraction pattern showed i) the only crystalline material present was a layered double hydroxide.

ii) there was a major line at 20 Å which was not present in the starting material.

v) Preparation of Mg/Al hydroxy sorbate.

Example 1 ii) was repeated except a solution comprising 45.05 g potassium sorbate dissolved in 500 ml water was added to 40 g of the nitrate formed in Example 1 i).

The chemical analysis of the resulting product was:

% MgO+Al$_2$O$_3$=40.08

% C=21.87

This is consistent with a formula for the anhydrous material of Mg$_4$ Al$_2$ (OH)$_{12}$ (sorbate)$_2$ The x ray diffraction pattern showed i) the only crystalline material present was a layered double hydroxide.

ii) there was a major line at 16.9 Å which was not present in the starting material.

IR analysis of the product showed absorption peaks centred at 1155 cm$^{-1}$, 1286 cm$^{-1}$, 1405 cm$^{-1}$, 1538 cm$^{-1}$, 1622 cm$^{-1}$ and 1652 cm$^{-1}$ which were not present in the nitrate starting material and are consistent with the presence of sorbate ions.

Example 2

Ion Exchange of Mg/Al Hydroxy Lactate with Oleate (Sodium Salts and Oleic Acid)

This example was carried out to simulate the interaction of a cosmetic composition according to the invention comprising Mg/Al hydroxy lactate with sebaceous acids and anionic derivatives (oleic acid and sodium oleate) present on the human skin.

0.5 g of Mg/Al hydroxy lactate, prepared as described above, was dispersed in 10 ml of distilled water in a glass beaker. The dispersion temperature was raised to 32° C., and then 12.5 ml of sodium oleate solution$^+$ (concentrations given in Table below), held at the same temperature, was added. The resulting suspension was stirred vigorously for 1 hour at 32° C. The resulting solid was filtered off, washed with warm water, and then freeze dried. The exchange solution was retained for analysis.

The solid product was characterised by XRD, and thermal and chemical analysis. The exchange solution was analysed for lactate ions using ion chromatography.

TABLE I

Experimental Conditions

| Code | Conc. sodium oleate sol.$^+$ | Molar ratio lactate in LDH$^{\ddagger}$ : oleate in solution |
|---|---|---|
| A | 0.125 molar | 1:1 |
| B | 0.063 molar | 1:0.5 |
| C | 0.031 molar | 1:0.25 |
| D | 0.013 molar | 1:0.1 |
| E | none | not applicable |

TABLE II

Analysis of Solid Product

| Code | Mole % oleate * | Basal spacing (XRD) |
|---|---|---|
| A | 89 | 32.5Å |
| B | 39 | 32.0Å |
| C | 15 | 14.8Å |
| D | 1 | 14.6Å |
| E | 0 | 14.6Å |

* mole % oleate = moles oleate/(moles oleate + moles lactate) × 100
$^{\ddagger}$Layered Double Hydroxide

TABLE III

Analysis of Exchange Solution

| Code | Lactate released into solution (% of total initially in the LDH) |
|---|---|
| A | 90% |
| B | 63% |
| C | 35% |
| D | 19% |
| E | 13% |

The results demonstrate that oleate is taken up by the hydroxy material at the expense of lactate which is released. Ion Exchange of Lactate LDH with Oleate (Oleic Acid)

0.5 g of Mg/Al hydroxy lactate prepared as described above was dispersed in 22.5 ml of distilled water in a glass bottle. The dispersion temperature was raised to 32° C., and then 0.442 g oleic acid was added. The resulting suspension was shaken vigorously for 10 minutes. The solid was filtered off, washed with ethanol and then warm water. It was then freeze dried.

The solid product was analyzed by XRD, thermal analysis and chemical analysis.

XRD of the product showed the only crystalline phase present was a layered double hydroxide with a basal spacing of 32 Å which is characteristic of uptake of oleate into the structure.

Thermal and chemical analysis of the product gave a mole % of oleate in the product of 65%, demonstrating that oleate had been taken up by the hydroxy material.

Example 3

Ion Exchange of Mg/Al Hydroxy Glycolate with Sodium Oleate

This example was carried out to simulate the interaction of a cosmetic composition according to the invention comprising Mg/Al hydroxy with sebaceous acids and anionic derivatives (sodium oleate) present on the human skin.

1 g of Mg/Al hydroxy glycolate, prepared as described above, was dispersed in 20 ml of distilled water in a glass beaker. The dispersion temperature was raised to 32° C., and then 25 ml of sodium oleate solution (+ for concentrations see Table below), held at the same temperature, was added. The resulting suspension was stirred vigorously for 15 minutes at 32° C. The resulting solid was filtered off, washed with warm water, and then freeze dried. The exchange solution was retained for analysis.

The solid product was characterised by XRD, and thermal and chemical analysis. The exchange solution was analyzed for lactate ions using ion chromatography.

TABLE IV

Experimental conditions

| Code | Conc. sodium oleate sol.+ | Molar ratio glycolate in LDH:oleate in solution |
|------|---------------------------|-------------------------------------------------|
| A    | 0.154 molar               | 1:1                                             |
| B    | 0.077 molar               | 1:0.5                                           |
| C    | 0.039 molar               | 1:0.25                                          |

TABLE V

Analysis of Solid Product

| Code | Mole % oleate* | Basal spacing (XRD) |
|------|----------------|---------------------|
| A    | 100            | 33.9Å               |
| B    | 58             | 36.9Å, 9.5Å         |
| C    | 25             | 9.7Å, 36.7Å         |

*mole % oleate = moles oleate/ (moles oleate + moles glycolate) × 100

TABLE VI

Analysis of Exchange Solution

| Code | Glycolate released into solution (% of total initially in the LDH) |
|------|--------------------------------------------------------------------|
| A    | 84%                                                                |
| B    | 66%                                                                |
| C    | 43%                                                                |

The results demonstrate that oleate is taken up by the hydroxy material at the expense of glycolate which is released.

Example 4

Various types of cosmetic compositions according to the invention were formulated as follows, where:

Carbomer is Carbopol 980 (Goodrich)
Cetearyl alcohol is Alfol 16-18 (Condea)
Ceteth-20 is Brij 58 (ICI)
Dimethicone is DC200 fluid (Dow Corning)
Glycerol is Pricerine 9058 (Unichema)
Glycerol monostearate is Estol 1473 (Unichema)
Isohexadecane is Arlamol HD (ICI)
Mica is Mica 280 (Whittaker Clark & Daniels)
Mineral oil is Sirius M85 (Silkolene)
PEG-40 hydrogenated castor oil is Cremophor RH 40 (BASF)
Polydecene dimer is Ethylflo 362 NF (Ethyl Corp)
Silica bead is Silica bead S-700 (Miyoshi Kasei Inc)
Talc is Suprafino A (Cyprus Ind Minerals)
Trideceth-12 is Renex 30 (ICI)
Triethanolamine was from BDH
Xanthan gum is Rhodopol (Rhone-Poulenc)
Zinc stearate is Zinc Stearate USP-D (Witco)

| COMPRESSED POWDER | |
|---|---|
| Talc | 34.25 |
| Mg/Al hydroxy lactate | 40.00 |
| mica 280 | 10.00 |
| Silica bead | 9.00 |
| Pigments | 0.50 |
| Zinc stearate | 3.00 |
| Dimethicone (dimethyl polysiloxane) | 3.00 |
| Preservative | 0.25 |

| LIQUID FOUNDATION | |
|---|---|
| Mineral oil | 10.00 |
| *Mg/Al hydroxy lactate | 10.00 |
| Cetearyl alcohol | 2.00 |
| Glycerol monostearate | 0.50 |
| Ceteth-20 (POE (20) hexadecyl ether) | 0.50 |
| Xanthan gum | 0.30 |
| Glycerol | 2.00 |
| Pigments | 8.44 |
| Preservative | 0.30 |
| Water* | 66.26 |

*In the above formulation the Mg/Al hydroxy lactate and water may be replaced by the following combination

| | % wt |
|---|---|
| Mg/Al hydroxy chloride | 8.46 |
| Sodium lactate | 4.50 |
| Water | 63.30 |

| MOISTURISING CREAM | |
|---|---|
| Mineral oil | 10.00 |
| Zn/Al hydroxy glycolate | 10.00 |
| Cetearyl alcohol | 2.00 |
| Glycerol monostearate | 0.50 |
| Ceteth-20 | 0.50 |
| Xanthan gum | 0.30 |
| Glycerol | 2.00 |
| Preservative | 0.30 |
| Water | 74.40 |

| CLEANSING CREAM | |
|---|---|
| Polydecene dimer | 20.00 |
| Isohexadecane | 10.00 |
| Mg/Al hydroxy lactate | 10.00 |
| PEG-40 hydrogenated castor oil | 2.00 |
| Trideceth-12 (POE(12) tridecyl ether) | 0.30 |
| Cetearyl alcohol | 3.00 |
| Preservative | 0.30 |
| Carbomer | 0.30 |
| Triethanolamine | 0.30 |
| Water | 53.80 |

We claim:

1. A cosmetic composition comprising from 0.1 to 100% by weight of the composition of a hydroxy material selected from:

a) layered double hydroxides of formula

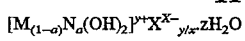  (I)

where
M is selected from divalent metal ions and lithium;
N is a trivalent metal ion;
X is an anion of charge x−;
y+ is the net charge on the mixed metal hydroxide cation; and
when M is a divalent metal ion a is a number from 0.17 to 0.5 and y=a;
when M is lithium a is a number from 0.67 to 0.75 and y=(2a−1); and
z is a number from 0 to 10; and b) a hydroxy salt of formula

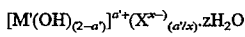  (II)

where
M' is at least one divalent metal ion;
a' is a number in the range 0.05 to 1;
X is an anion of charge x−; and
z is a number from 0 to 10; or a c) mixture thereof and
wherein X is trichloro-2hydroxy diphenyl ether
wherein the hydroxy material releases the skin benefit agent via ion exchange.

2. A method of treating the skin with the hydroxy material of claim 1 which comprises applying an effective amount of said hydroxy material to the skin.

* * * * *